(12) United States Patent
Doerge et al.

(10) Patent No.: US 11,161,165 B2
(45) Date of Patent: Nov. 2, 2021

(54) PROCESSES FOR PRODUCING A SLEEVE FOR AN ELECTRODE FOR MEDICAL APPLICATIONS

(71) Applicant: Heraeus Deutschland GmbH & Co. KG, Hanau (DE)

(72) Inventors: Thomas Doerge, Neunkirchen (DE); Christiane Leitold, Wölfersheim (DE); Oliver Keitel, Aschaffenburg (DE); Dominik Schneider, Geiselbach (DE); Katharina Musiol, Hanau (DE); Josef Roth, Bessenbach (DE); Bernd Koch, Wuppertal (DE); Benjamin Koch, Wuppertal (DE); Herwig Schiefer, Frankfurt (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 1385 days.

(21) Appl. No.: 15/356,350

(22) Filed: Nov. 18, 2016

(65) Prior Publication Data

US 2017/0143220 A1    May 25, 2017

(30) Foreign Application Priority Data

Nov. 19, 2015 (EP) ..................................... 15195313

(51) Int. Cl.
*B21D 35/00* (2006.01)
*B21D 28/06* (2006.01)
(Continued)

(52) U.S. Cl.
CPC ........... *B21D 35/001* (2013.01); *B21D 22/02* (2013.01); *B21D 28/06* (2013.01); *B21D 51/54* (2013.01);
(Continued)

(58) Field of Classification Search
CPC ...... B21D 35/001; B21D 22/02; B21D 28/06; B21D 51/54; Y10T 29/49204;
(Continued)

(56) References Cited

U.S. PATENT DOCUMENTS

| | | | | |
|---|---|---|---|---|
| 2,610,390 A | * | 9/1952 | Locke ..................... | B21D 53/36 29/874 |
| 5,178,607 A | * | 1/1993 | Lynn .................. | A61B 5/15003 600/575 |

(Continued)

FOREIGN PATENT DOCUMENTS

| EP | 1323483 | 7/2003 |
|---|---|---|
| EP | 2772280 | 9/2014 |

(Continued)

*Primary Examiner* — Peter Dungba Vo
*Assistant Examiner* — Azm A Parvez
(74) *Attorney, Agent, or Firm* — Dicke, Billig & Czaja, PLLC (57) ABSTRACT

One aspect relates to a method of producing a sleeve for a ring electrode for electrophysiological and neuro-medical applications from a biocompatible metallic tape. Repetitive structures are punched into the tape and each includes at least one surface that is connected by at least one fin to at least one external strip. The at least one external strip connects the repetitive structures to each other on the margin. A sleeve mold is formed from a multiple of the repetitive structures through multiple reforming steps by a reforming technique. The sleeve mold is punched off the such that the sleeve is formed with a first tube-shaped region with a larger diameter and a second tube-shaped region with a smaller diameter. The first region with the larger diameter has a larger external diameter and internal diameter than the second region with the smaller diameter, and the two regions are connected.

19 Claims, 10 Drawing Sheets

(51) Int. Cl.
*B21D 51/54* (2006.01)
*B21D 22/02* (2006.01)

(52) U.S. Cl.
CPC ... *A61B 2562/125* (2013.01); *Y10T 29/49204* (2015.01)

(58) Field of Classification Search
CPC ......... Y10T 29/49211; Y10T 29/49213; Y10T 29/49117; Y10T 29/49002
USPC .................. 29/879, 878, 874, 825, 592.1
See application file for complete search history.

(56) References Cited

U.S. PATENT DOCUMENTS

| | | | |
|---|---|---|---|
| 2003/0211352 A1* | 11/2003 | Ooyauchi | B21C 37/0803 428/600 |
| 2005/0126666 A1* | 6/2005 | Zhu | C22F 1/183 148/670 |
| 2012/0157879 A1* | 6/2012 | Mark | A61B 10/0275 600/566 |
| 2013/0225957 A1* | 8/2013 | Kawamoto | A61B 5/14865 600/347 |
| 2015/0148879 A1 | 5/2015 | Rump et al. | |
| 2015/0223713 A1* | 8/2015 | Ollivier | H01R 43/20 600/374 |

FOREIGN PATENT DOCUMENTS

| | | |
|---|---|---|
| EP | 2875844 | 5/2015 |
| JP | 5829598 | 2/1983 |

* cited by examiner

PROCESSES FOR PRODUCING A SLEEVE FOR AN ELECTRODE FOR MEDICAL APPLICATIONS

CROSS-REFERENCE TO RELATED APPLICATIONS

This Utility patent application claims priority to European Patent Application No. EP 15195313.0, filed on Nov. 19, 2015, which is incorporated herein by reference.

BACKGROUND

One aspect relates to processes for producing a metallic sleeve as ring electrode for electrophysiological and neuro-medical applications as well as processes for producing a neuro-medical sensor or an electrophysiological ring electrode using said method for producing the sleeve. One aspect also relates to a sleeve produced with a process of this type.

In cardiac rhythm management (CRM) or electrophysiology and neuro-medicine, ring electrodes made of precious metal are used for stimulation and/or recording of bioelectrical signals. Typically, said ring electrodes are produced by a turning process ("Swiss machining") in the form of sleeves structured as continuous tubes and need to be fabricated from a rod or the like with a large loss of precious metal. Moreover, the process is expensive and laborious due to the long requisite processing times. Only approximately one sleeve per two to three minutes can be fabricated in a turning process. Moreover, the process is limited with respect to very thin wall thicknesses, which cannot be fabricated by means of a turning process without additional effort. Moreover, the tools (for example, the milling heads or cutting tools) are subject to wear and tear while turning the excess material and need to be replaced in regular intervals. In addition, the turning process is subject to major variation due to the wear-and-tear of tools. Consequently, this process is subject to major variation of the component geometry.

A ring electrode for electrical neuro-stimulation is known from US 2015/0223713 A1. In this context, a sleeve is used in the form of a carrier tube with different external diameters to bear a chip as sensor and to connected it to electrical leads. The structure of the sleeve is difficult to implement and cannot be fabricated by turning alone.

EP 2 875 844 A1 discloses a ring electrode for electrophysiological and/or neuro-medical stimulation and measurement of electrical signals in the body. Another ring electrode is known from EP 2 772 280 A1. In this context, the ring electrode is made up of sleeves that include two ends with different external diameters and are electrically contacted by means of helically coiled connecting wires. Another helically coiled cable is guided, as internal coil, through the inside of the sleeves and has a tip electrode contacting it by means of which an electrical impulse, as pacemaker, can be administered.

The sleeves are processed out of massive precious metal bodies by turning or other cutting procedures. This is associated with a major effort in order to be able to produce the sleeves at the desired accuracy. Moreover, large amounts of precious metal waste are produced that need to be reprocessed in laborious manner. Processes of this type are unsuitable for a rapid and inexpensive mass production.

For these and other reasons, a need exists for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The embodiments will now be detailed by way of exemplary embodiments with reference to the attached drawings.

Exemplary embodiments shall be illustrated in the following on the basis of ten schematic figures, though without limiting the scope of the invention.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present embodiments will now be described in detail with reference to the figures, it is done so in connection with the illustrative embodiments and is not limited by the particular embodiments illustrated in the figures, as defined by the appended claims.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described.

Because components of embodiments can be positioned in a number of different orientations, the directional terminology is used for purposes of illustration and is in no way limiting. It is to be understood that other embodiments may be utilized and structural or logical changes may be made without departing from the scope of the embodiments. The following detailed description, therefore, is not to be taken in a limiting sense, and the scope of the invention is defined by the appended claims.

It is to be understood that the features of the various exemplary embodiments described herein may be combined with each other, unless specifically noted otherwise.

One aspect overcomes the disadvantages of the prior art. For example, a process for producing a sleeve for a ring electrode for electrophysiological and neuro-medical applications is to be provided, whereby the process is to be simple, rapid and inexpensive to implement. Moreover, the process is to be implemented inexpensively and is to produce only a minimized amount of precious metal waste. In addition, the process shall be rapid to implement to produce sleeves at the requisite accuracy in the shortest possible time. Due to the low amounts and due to the sleeves being variable as they can be used for different purposes, it should be possible to easily and rapidly modify the method by means of modifying the structure and/or the machine by means of which the process is implemented such that the produced sleeve mold can be varied and/or modified. Moreover, the risk of the wires for electrical contacting of the ring electrode and sleeve being subject to adverse influences during the subsequent continued processing shall be as low as possible. The structure and the shape of the sleeve shall already be suitable for this purpose.

Figure 1:
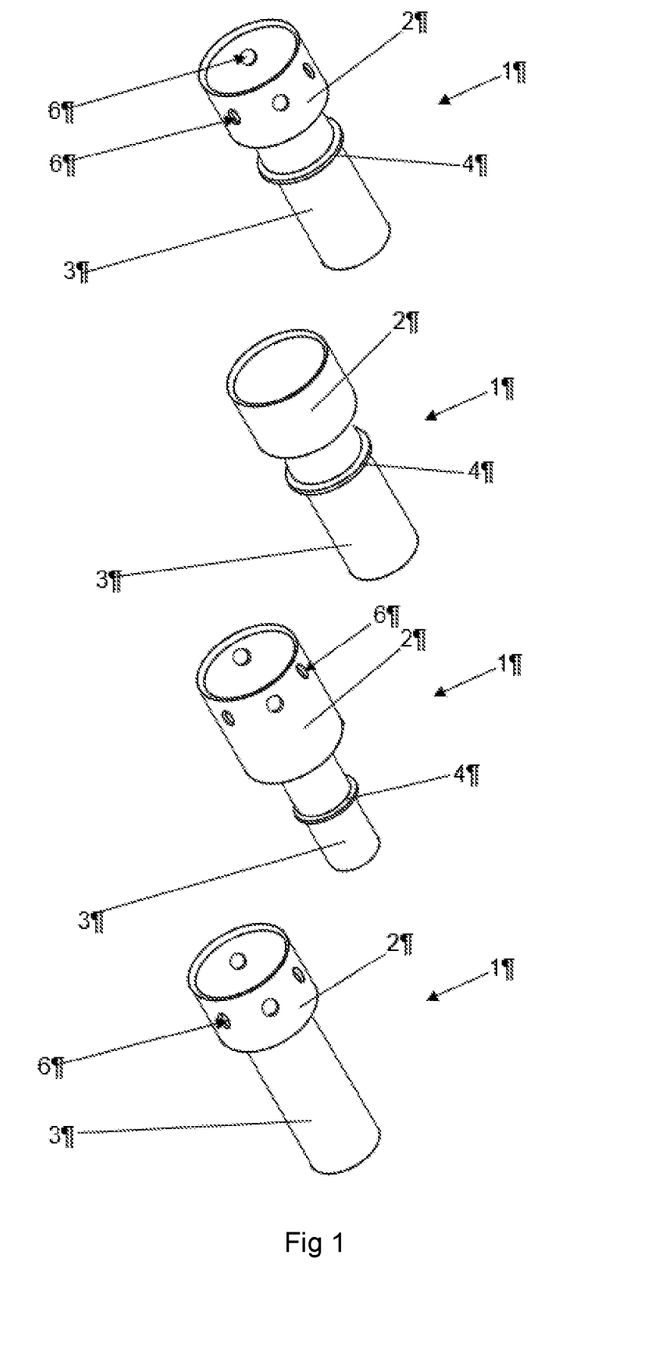
FIG. 1 illustrates a schematic perspective view of four sleeves according to one embodiment that were produced using a process according to one embodiment.

FIG. 1 illustrates a schematic perspective view of four different sleeves 1 that can be produced with processes according to one embodiment. Each sleeve 1 comprises a first region 2 with a larger diameter and a second region 3 with a smaller diameter. The sleeves 1 form continuous tubes, whereby the internal diameter in the first region 2 is larger than the internal diameter in the second region 3. As a matter of rule, the sleeves 1 include the same wall thickness of between 0.01 mm and 0.1 mm and consist of a precious metal such as, for example and according to one embodiment, platinum or of a precious metal compound such as, for example and according to one embodiment, a platinum-iridium alloy.

A flange 4 can be provided in the second region 3 that fully extends around the second region 3 as an elevation above the external diameter of the second region 3. A flange 4 of this type can be generated, for example, by some kind of pleating during a deep-drawing step or two deep-drawing steps during a stepwise reforming from a two-dimensional metallic starting material (the precious metal or precious metal compound). Recesses 6 can be provided in the first region 2 and can extend in the first region 2 into the inside of the sleeve 1. In addition, embossed depressions (not illustrated) can be present. Later on, the depressions serve as elastic fastening elements for hose jackets and can be generated by denting from the direction of the cylinder jacket wall in the first region 2. The recesses 6 can also be provided in the depressions. The recesses 6 perforate the wall of the first region 2. The recesses 6 can be generated by punching or the recesses 6 a generated concurrently with the depressions through a joined punching-deep-drawing step, in which a tool module suitable for punching and deep-drawing is used.

With the exception of the recesses 6 and possibly the depressions, the sleeves 1 are designed to be rotationally symmetrical with respect to a cylinder axis that extends in the direction of the through-going opening of the tube formed by the sleeve 1. For production and application of the ring electrode, the flange 4 or the flank between the first region 2 and the second region 3 can later have wires (not illustrated) for electrical contacting of the sleeve 1 welded to them.

Figure 2:
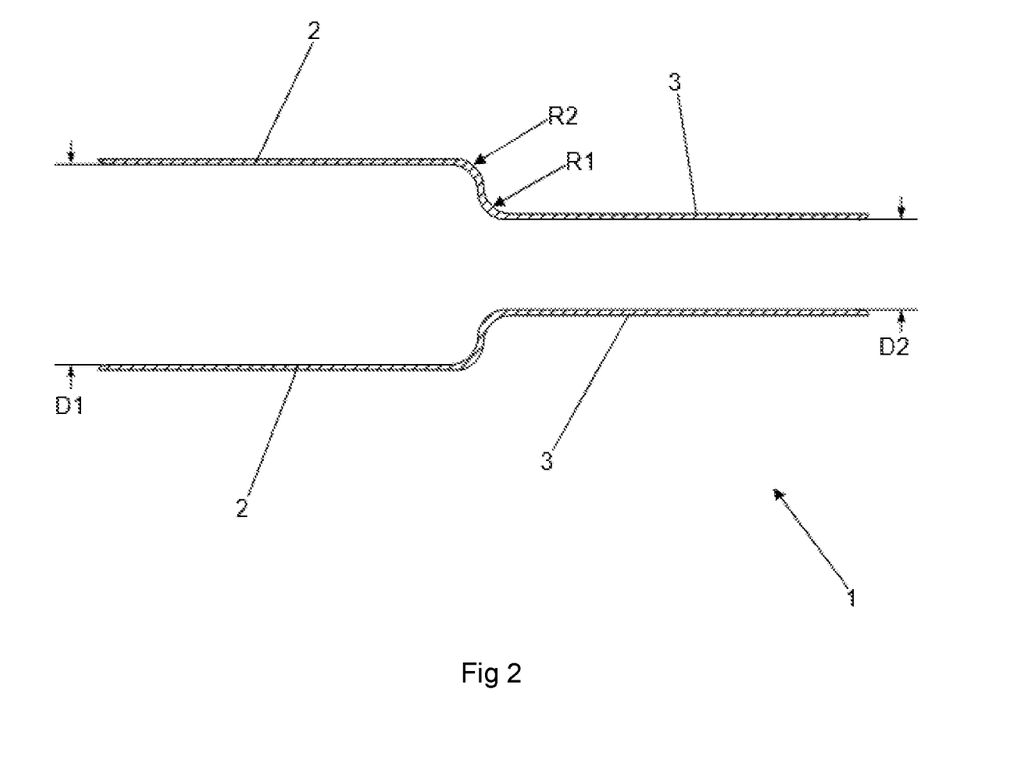
FIG. 2 illustrates a schematic cross-sectional view of a sleeve according to one embodiment that was produced using a process according to one embodiment.
Figure 3:
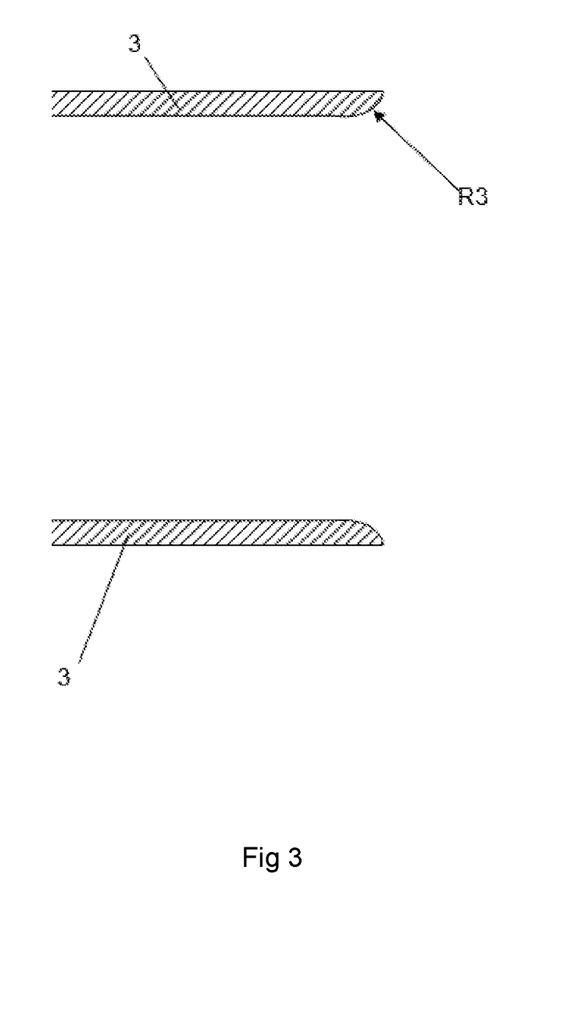
FIG. 3 illustrates a partial view of the schematic cross-sectional view according to FIG. 2, in which the smaller region of the sleeve and the bevel of the edges are illustrated.

FIG. 2 illustrates a schematic cross-sectional view of a sleeve 1 according to one embodiment that was produced with a process according to one embodiment, and FIG. 3 illustrates a partial view of the schematic cross-sectional view according to FIG. 2, in which the smaller second region 3 of sleeve 1 and the bevel of the edges with a radius R3 are illustrated. The diameter D1 of the sleeve 1 in the first region 2 is larger than the diameter D2 in the second region 3. Due to the reforming taking place by deep-drawing, no sharp edges, which might lead to an adverse effect on wires (not illustrated) to be connected to sleeve 1, arise at the transitions between the first region 2 and the second region 3. Instead, radii of curvature R1 and R2 of at least 0.1 mm or, in one embodiment, of at least 0.5 mm are generated that do not or do not easily lead to mechanical damage to the wires. In addition, it is clearly evident from FIG. 2 that the sleeve 1 comprises a through-going opening (from left to right in FIG. 2).

Likewise, the edges of the sleeve 1 are rounded, as is seen particularly well in FIG. 3. The corresponding radius of curvature R3 also is at least 0.1 mm such that the risk of damage to the wires contacting sleeve 1 is reduced at this site as well.

Figure 4:
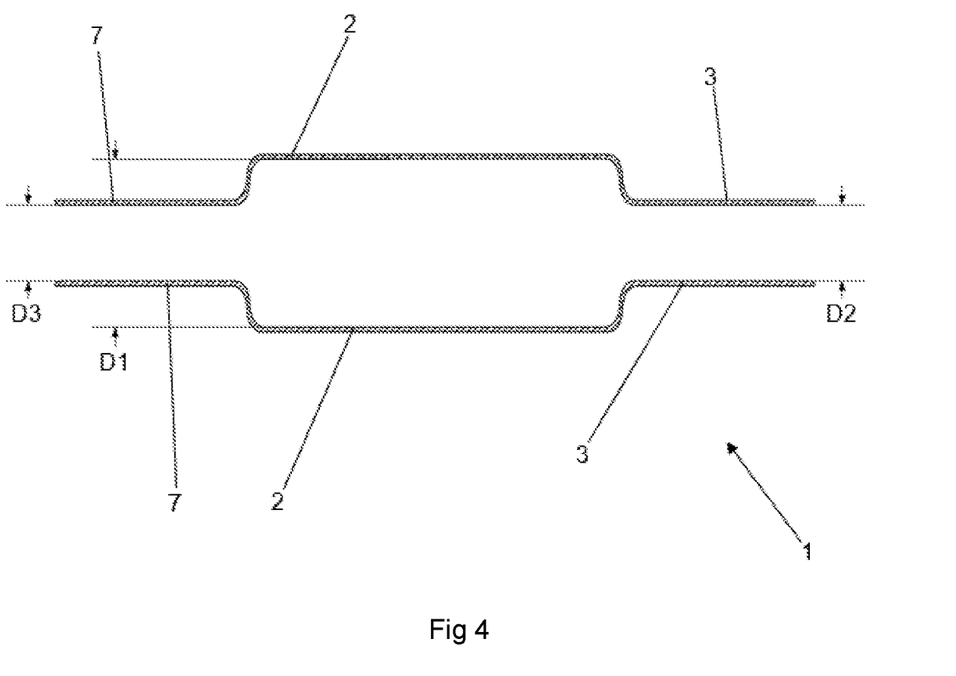
FIG. 4: illustrates a schematic cross-sectional view of another sleeve according to one embodiment, with three regions, that was produced using a process according to one embodiment.

FIG. 4 illustrates a schematic cross-sectional view of another sleeve 1 according to one embodiment that was produced using a process according to one embodiment. The sleeve 1 includes a first region 2 with a larger diameter and a second region 3 with a smaller diameter as well as a third region 7 with a smaller diameter. The internal diameter D1 of the first region 2 is larger than the internal diameters D2 and D3 of the second region 3 and third region 7, respectively. The internal diameter D2 of the second region can be larger, equal in size or smaller than the internal diameter D3 of the third region 7.

The sleeve 1 forms a continuous tube. As a matter of rule, the sleeve 1 has a uniform wall thickness of between 0.01 mm and 0.1 mm and consists of a precious metal or of an inter-metallic alloy containing a precious metal as its main component. The radii of curvature at the transitions from the second region 3 to the first region 2 and from the first region 2 to the third region 7 are formed appropriately such that they are at least 0.1 mm. Wires (not illustrated) can be guided through the continuous sleeve. Moreover, the sleeve 1 itself can be electrically contacted to a wire (not illustrated) in order to form an electrophysiological electrode.

Figure 8:
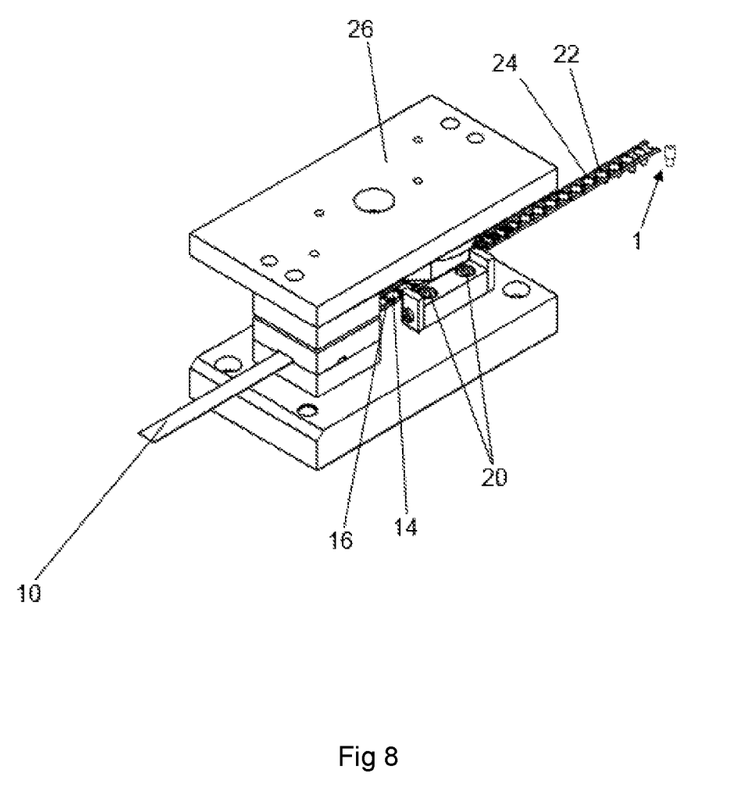
FIG. 8: illustrates a schematic perspective view of a machine for performing a process according to one embodiment.
Figure 9:
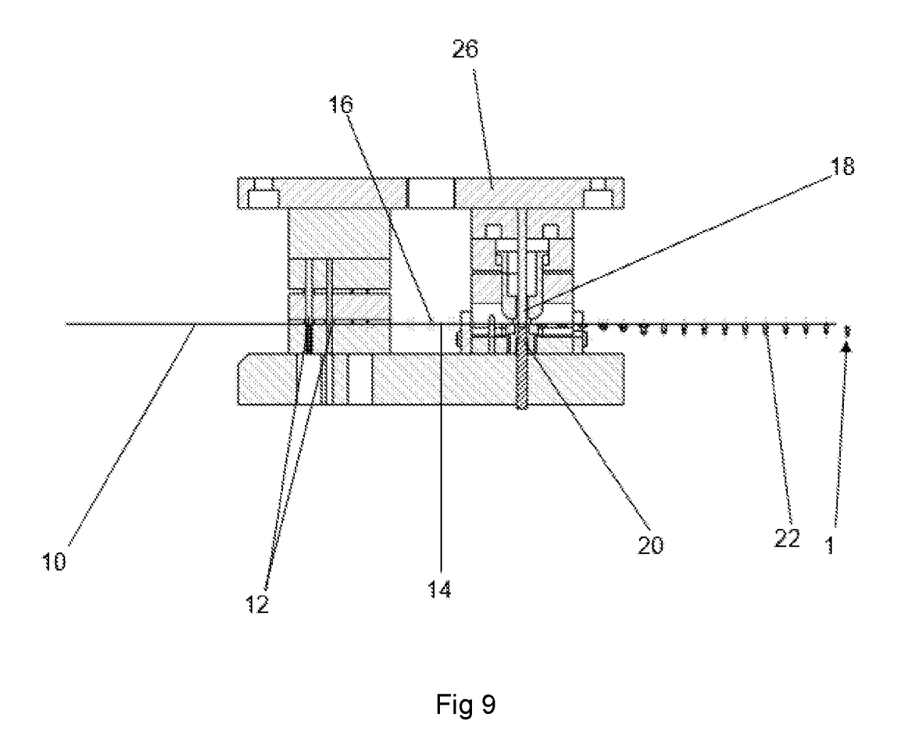
FIG. 9: illustrates a schematic cross-sectional view of the machine according to FIG. 8.
Figure 10:
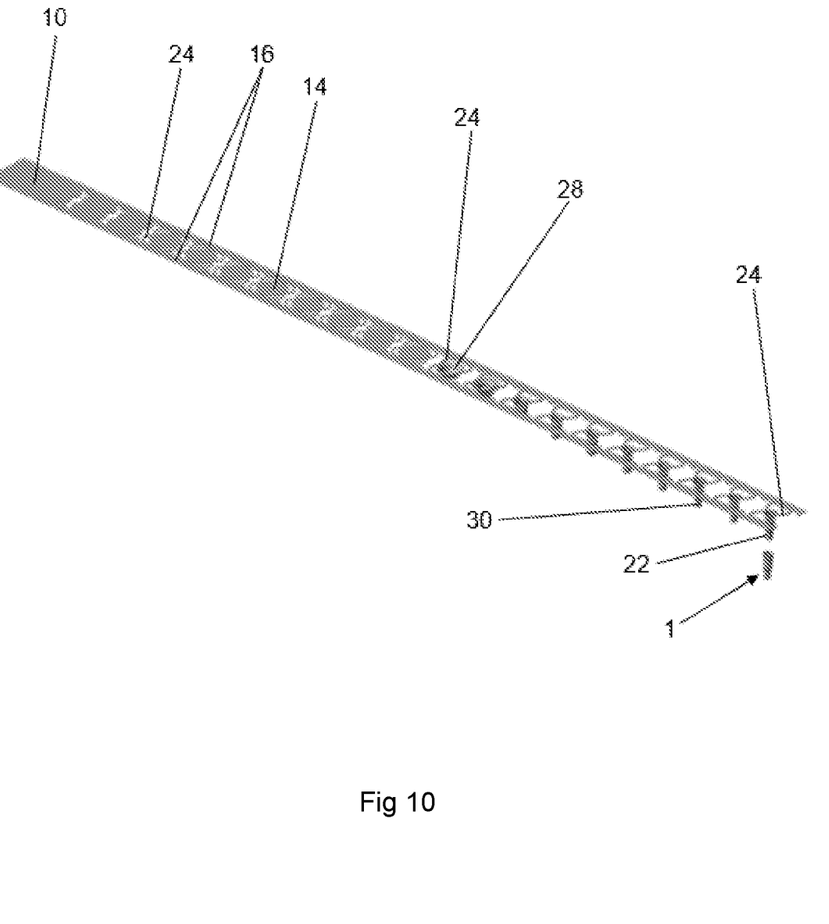
FIG. 10: illustrates a schematic perspective view of a tape during reforming by a process according to one embodiment.

During the production of the sleeve 1 according to FIG. 4, the first region 2 is deep-drawn first from a surface of a tape (see FIGS. 8 to 10). Subsequently, the second region 3 is generated by deep-drawing in the first region 2. These two deep-drawing steps can take place in the form of multiple separate reforming steps by applying punches to the surface perpendicular to the surface from which the regions 2, 3 are deep-drawn. Subsequently, the third region 7 can be formed from the first region 2 by deep-drawing by pressing onto the side walls of the first region 2. As the final step, the sleeve mold is punched off such that the sleeve 1 according to FIG. 4 is present.

Figure 5:
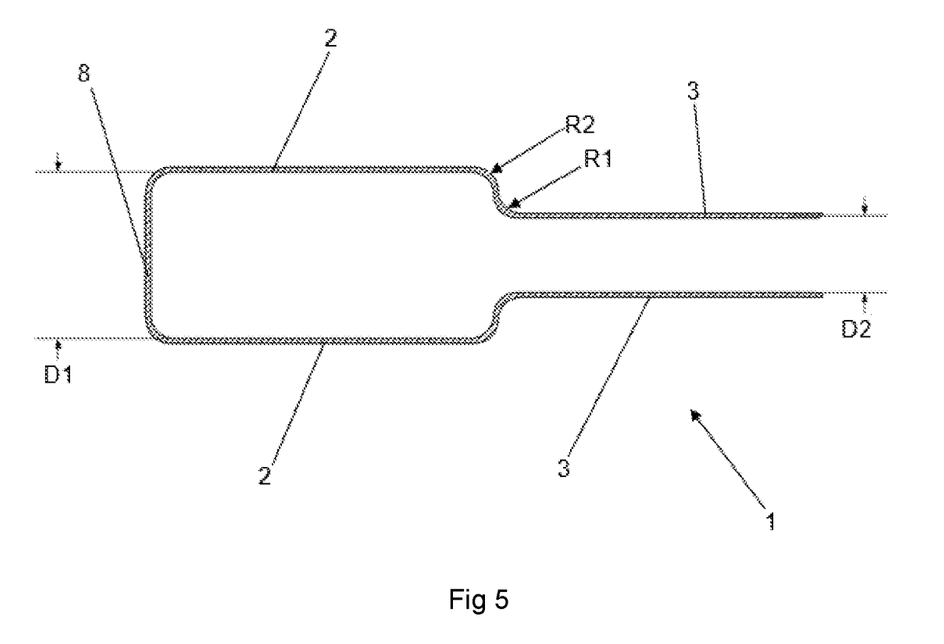
FIG. 5: illustrates a schematic cross-sectional view of another sleeve according to one embodiment, with a closed covering surface, that was produced using a process according to one embodiment.

FIG. 5 illustrates another schematic cross-sectional view of another sleeve 1 according to one embodiment with a closed covering surface 8 that was produced using a process according to one embodiment. The sleeve 1 includes a first region 2 with a larger diameter and a second region 3 with a smaller diameter. The internal diameter D1 of the first region 2 is larger than the internal diameter D2 of the second region 3.

The sleeve 1 forms a tube that is closed on one side. As a matter of rule, the sleeve 1 has a uniform wall thickness of between 0.01 mm and 0.1 mm and consists of tantalum, titanium, a precious metal or of an inter-metallic alloy that contains or is made of these. The radii of curvature R1, R2 at the transitions of the second region 3 to the first region 2 are appropriately shaped such that they are at least 0.1 mm. A wire (not illustrated) can be inserted into the sleeve 1 and electrically contacted in order to form an electrophysiological electrode.

During the production of the sleeve 1 according to FIG. 5, the first region 2 is deep-drawn first from a surface of a tape (see FIGS. 8 to 10). This deep-drawing step can take place in the form of multiple separate reforming steps by applying punches to the surface perpendicular to the surface from which the first region 2 is being deep-drawn. Subsequently, the third region 3 can be formed from the first region 2 by deep-drawing by pressing onto the side walls of the first region 2. As the final step, the sleeve mold is punched off such that the sleeve 1 according to FIG. 5 is present. In this context, the covering surface 8 remains closed and is not punched off.

Figure 6:
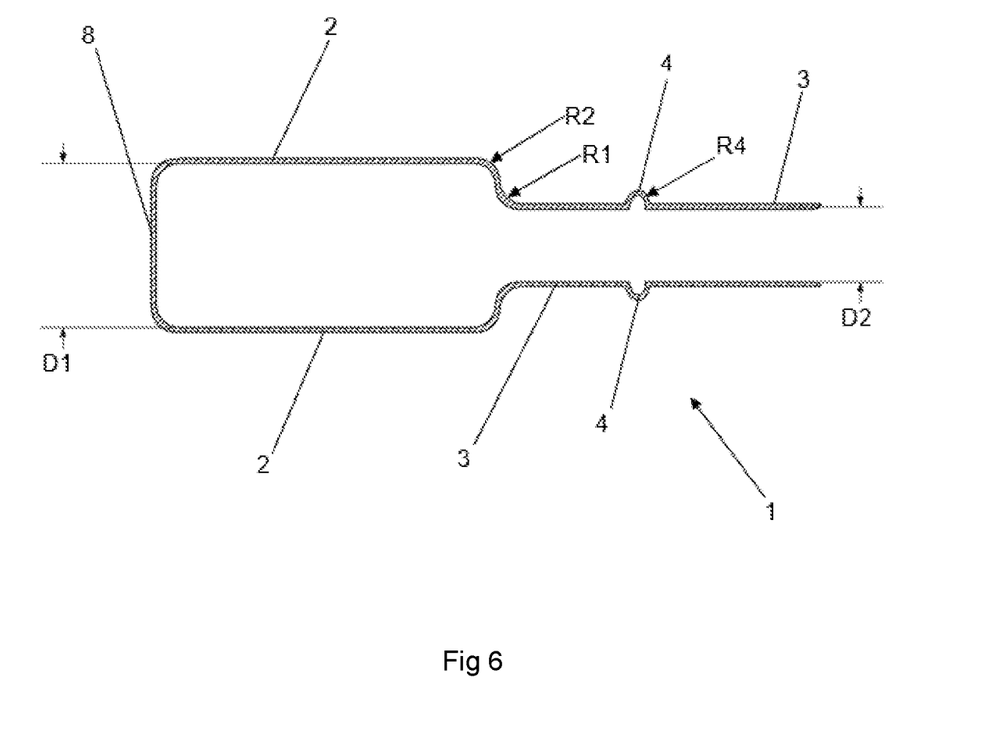
FIG. 6: illustrates a schematic cross-sectional view of another sleeve according to one embodiment, with a closed covering surface and flange, that was produced using a process according to one embodiment.

FIG. 6 illustrates a schematic cross-sectional view of another sleeve 1 according to one embodiment with a closed covering surface 8 and flange 4 that was produced using a process according to one embodiment; the sleeve 1 includes a first region 2 with a larger diameter and a second region 3 with a smaller diameter. The internal diameter D1 of the first region 2 is larger than the internal diameter D2 of the second region 3. A circumferential flange 4 that is elevated over the external diameter of the second region 3 is formed in the second region 3 of the sleeve 1.

The sleeve 1 forms a tube that is closed on one side. As a matter of rule, the sleeve 1 has a uniform wall thickness of between 0.01 mm and 0.1 mm and consists of tantalum, titanium, a precious metal or of an inter-metallic alloy that contains or is made of these. The radii of curvature R1, R2 at the transitions from the second region 3 to the first region 2 and the outward-facing radii of curvature R4 of the flange 4 are formed appropriately such that they are at least 0.1 mm. A wire (not illustrated) can be inserted into the sleeve 1 and electrically contacted in order to form an electrophysiological electrode.

During the production of the sleeve 1 according to FIG. 6, the first region 2 is deep-drawn first from a surface of a tape (see FIGS. 8 to 10). This deep-drawing step can take place in the form of multiple separate reforming steps by applying punches to the surface perpendicular to the surface from which the first region 2 is being deep-drawn. Subsequently, the third region 3 can be formed from the first region 2 by deep-drawing by pressing onto the side walls of the first region 2. Subsequently or concurrently, the flange 4 is generated in known manner by deep-drawing. As the final step, the sleeve mold is punched off such that the sleeve 1 according to FIG. 6 is present. In this context, the covering surface 8 remains closed and is not punched off.

Figure 7:
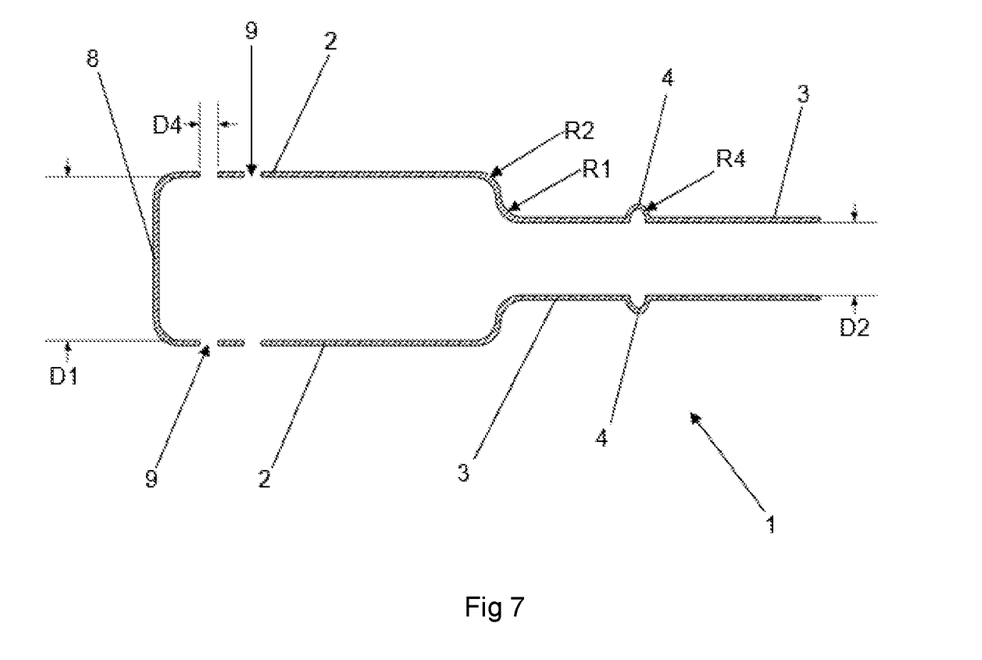
FIG. 7: illustrates a schematic cross-sectional view of another sleeve according to one embodiment, with a closed covering surface, flange, and recesses, that was produced using a process according to one embodiment.

FIG. 7 illustrates a schematic cross-sectional view of another sleeve 1 according to one embodiment with a closed covering surface 8, flange 4 and recesses 9 that was produced using a process according to one embodiment. The sleeve 1 includes a first region 2 with a larger diameter and a second region 3 with a smaller diameter. The internal diameter D1 of the first region 2 is larger than the internal diameter D2 of the second region 3. A circumferential flange 4 that is elevated over the external diameter of the sleeve 1 is formed in the second region 3 of the sleeve 1.

The sleeve 1 forms a tube that is closed on one side. As a matter of rule, the sleeve 1 has a uniform wall thickness of between 0.01 mm and 0.1 mm and consists of tantalum, titanium, a precious metal or of an inter-metallic alloy that contains or is made of these. The radii of curvature R1, R2 at the transitions from the second region 3 to the first region 2 and the outward-facing radii of curvature R4 of the flange 4 are formed appropriately such that they are at least 0.1 mm. A wire (not illustrated) can be inserted into the sleeve 1 and electrically contacted in order to form an electrophysiological electrode.

During the production of the sleeve 1 according to FIG. 6, the first region 2 is deep-drawn first from a surface of a tape (see FIGS. 8 to 10). This deep-drawing step can take place in the form of multiple separate reforming steps by applying punches to the surface perpendicular to the surface from which the first region 2 is being deep-drawn. Subsequently, the third region 3 can be formed from the first region 2 by deep-drawing by pressing onto the side walls of the first region 2. Subsequently or concurrently, the flange 4 is generated in known manner by deep-drawing. As the final step, the sleeve mold is punched off such that the sleeve 1 according to FIG. 6 is present. In this context, the covering surface 8 remains closed and is not punched off.

Moreover, a multitude of recesses 9 have been punched into the wall of the first region 2 in the embodiment according to FIG. 7. These can serve, for example, to allow a liquid to flow through the sleeve 1 and the recesses 9. The liquid can be used for cooling a ring electrode produced to include the sleeve 1. The recesses 9 or some of the recesses 9 can be used alternatively for the fastening of components such as wires (not illustrated) or insulation hoses (not illustrated) of the electrophysiological electrode.

The edges of the sleeves 1 according to FIGS. 4 to 7 are designed analogous to FIG. 3.

FIG. 8 illustrates a schematic perspective view of the main parts of a machine intended for implementing a process according to one embodiment. FIG. 9 illustrates a corresponding schematic cross-sectional view of the machine according to FIG. 8. The reforming of the tape 10 is illustrated separately in a perspective view of the tape 10 in FIG. 10. FIGS. 8 and 9 thus illustrate a schematic view of a tool by means of which the tape 10 can be reformed. The first tool part and/or the first tool (left) serves for punching structures into the tape 10 and the second tool part and/or the second tool serves for reforming of the tape 10 that has been pre-formed by punching.

A metallic tape 10 made of a precious metal or an alloy, for example a compound with a precious metal as its main component, is conveyed through the machine and processed in the process, and/or the tape 10 is reformed in multiple steps in order to produce a sleeve 1 from it. FIGS. 8 and 9 illustrate the tape 10 during the reforming with a process according to one embodiment in order to provide a better overview of the individual steps of reforming of the tape 10 for production of the sleeve 1.

In a first part of the machine (on the left in FIGS. 8 and 9), the tape 10 is being processed using multiple punches 12. In this context, parts of the tape 10 are punched out in order to generate repetitive structures in the tape 10, which are reformed into sleeves 1 later on. More than just the punching steps may take place just as well. Theoretically, it is feasible to perform the punching of the repetitive structures in just a single step with a single punching module of the first part of the machine. After the punching, repetitive structures (see FIG. 10 also) are formed in the tape 10, whereby each repetitive structure includes an internal surface 14 in the form of a circular disk with a diameter of 5 to 20 mm, depending on the sleeve 1 to be produced. Each internal surface 14 is connected by four fins 24 to two external strips 16 that flank the internal surface 14 on both sides and keep the tape 10 together. It needs to be noted in this context that the structuring of the tape 10 is indicated only by vertical auxiliary lines in FIG. 9 due to it being a side view.

In a second part (on the right in FIGS. 8 and 9) of the machine, the inner surfaces 14 of the tape 10 are reformed in stepwise manner by deep-drawing through the use of multiple modules of which only one is illustrated in FIG. 9 for purposes of clarity, using one punch 18 each and one press mold 20 each. The individual stages and/or steps of reforming can be seen particularly well in FIG. 10. Due to the deep-drawing with the modules in multiple steps, a sleeve mold 22 is generated and/or processed further that remains connected to the external strips 16 by the pins 24 such that the tape 10 can be conveyed and processed easily in the machine. The two parts of the machine are pressed together by an automatic press 26. Between the individual steps of reforming, the tape 10 is appropriately transported further such that the repetitive structures and/or the sleeve molds 22 are transported further to the next module, that is, for example exactly by the length of one of the repetitive structures of the tape 10. The sleeve mold 28 (see FIG. 10) is reformed only little after the first deep-drawing step, whereas the sleeve mold 30 (see FIG. 10) is fully formed, except for the closed bottom, after the final deep-drawing step. The initially closed bottom of the lower part (of the second region 3 according to FIGS. 1 and 3) of the sleeve mold 30 is punched off with another punch (not illustrated) or is cut open by means of a laser or other process. Subsequently, the finished sleeve mold 22 is punched off, i.e. the fins 24 are severed in the region of the sleeve mold 22. The finished sleeve 1 can then be used as a ring electrode and can be electrically contacted to wires (not illustrated).

Due to the reforming of the tape 10 through deep-drawing steps, sleeves 1 are generated that have a radius of curvature R1, R2 of at least 0.1 mm such that no damage to the wires by sharp edges of the sleeves 1 can occur when the sleeves 12 are subsequently contacted to wires (not illustrated). At the same time, the tape 10 and the tool as well as the modules in it can be used to produce a large number of sleeves 1 inexpensively and in a short period of time. Due to the variably usable modules and the step-wise reforming, the machine is easy to convert to different types of sleeves 1, as are illustrated, for example, in FIG. 1. In this context, to some extent, the same modules can be used for different sleeves 1 which reduces the costs and the effort involved in the conversion.

One embodiment can provide the ends and/or edges of the sleeves 1 to be beveled or embossed by the reforming to have a radius of curvature R3 such that sharp edges are prevented at these sites as well.

The features disclosed in the preceding description and in the claims, figures, and exemplary embodiments, can be important for the implementation of the various embodiments both alone and in any combination.

One embodiment includes a process for producing a sleeve for designing a ring electrode for electrophysiological and neuro-medical applications from a metallic tape, whereby the tape and the sleeve fabricated from it consist of a biocompatible metal or a biocompatible metallic compound, characterized in that repetitive structures are being punched into the tape, whereby the repetitive structures each include at least one surface that is connected by at least one fin to at least one external strip, whereby at least the at least one external strip connects the repetitive structures to each other on the margin, subsequently multiple of the at least one surfaces of the repetitive structures are made into a sleeve mold through multiple reforming steps by deep-drawing and/or another reforming technique, and the sleeve mold is then punched off such that the sleeve includes a first tube-shaped region with a larger diameter and a second tube-shaped region with a smaller diameter, whereby the first region with the larger diameter includes a larger external diameter and internal diameter than the second region with the smaller diameter, and the two regions are connected to each other in one-part manner.

One embodiment can provide the second region with the smaller diameter and the two regions to be appropriately connected to each other in one-part manner such that the sleeve forms a continuous tube or forms a tube that is closed on one side. One embodiment can just as well provide the tube to be closed on one side by a covering surface.

In this context, one embodiment can provide the external diameter of the first region with the larger external diameter to be at least 0.1 mm larger than the external diameter of the second region with the smaller external diameter.

One embodiment proposes that the tape and the sleeve fabricated from it consist of a precious metal, titanium, tantalum or a metallic compound thereof or a metallic compound containing at least one precious metal as main component or titanium or tantalum as main component.

The materials are particularly well-suited for the design of electrophysiological electrodes in medicine due to their chemical resistance.

A main component of a metallic compound shall presently be understood to mean that at least 50% by weight of the compound consist of a precious metal or a mixture of precious metals or of titanium or of tantalum. Moreover, the metal or the metallic compound must be biocompatible such that no poisoning or other adverse effect on the body of the patient can take place. Moreover, the compound must be metallic, that is, must be neither semi-conductive nor insulating at room temperature. In one embodiment, an inter-metallic alloy is used as metallic compound as the material for the metallic tape.

The finished sleeve can be open on both sides or closed on one side. The sleeve mold can be punched off, for example by the fins being severed right at the pre-shaped sleeve mold. Moreover, a closed covering surface of the sleeve and/or of the sleeve mold can be opened by the punching step.

For electrophysiological and neuro-medical applications, it is important that the material from which the sleeves are fabricated is biocompatible. In addition, the material of the sleeves should be chemically inert and/or as resistant as possible in order to prevent any change of the electrical properties of the sleeve and to be able to exclude any poisoning or adverse effect on the surrounding tissue. For example, precious metals are suited for this purpose, for example, palladium, platinum, gold as well as platinum and gold alloys such as, for example, platinum-rhodium or platinum-iridium alloys.

In one embodiment, the at least one of the surfaces of the repetitive structures are situated on the inside with respect to the punch-out tape and, for example, are flanked on the side by two external strips that extend on the margin of the tape over several of the repetitive structures. Moreover, one embodiment can provide that the at least one of the surfaces of the structures are connected to one external strip, in one embodiment to at least two external strips, by means of at least two, more by means at least three fins, and in one embodiment by means of four fins. The preceding measures increase the stability of the punched tape and thus simplify the further processing. It is also preferred in one embodiment that for the at least one of the surfaces to be circular or of an appropriate shape such that the ratio of the largest cross-section of the surface without the fins and the smallest cross-section of the surface is no more than 3, or is no more than 2, and in one embodiment is no more than 1.5. At least the surfaces of the tape consist of the metal and/or the metallic alloy, and in one embodiment the entire tape consists of the metal or the metallic alloy as this renders the tape easy to process. Alternatively, the at least one external strip and/or the at least one fin can consist of a plastic material or any other material that is connected to the metallic tape or the metallic alloy, is laminated to it. This allows even a little more precious metal to be saved, but it renders the production of the tape somewhat more laborious. The punching in this embodiment can include the plastic strip on the metallic tape to be shaped by punching.

One embodiment can provide for multiple surfaces to be provided and/or punched in next to each other in each of the repetitive structures in the metallic tape, whereby the surfaces arranged next to each other are connected to each other by means of fins. In this context, the external surfaces are connected by means of fins to strips on the side that extend along the tape perpendicular to the services of the repetitive structures. As a result, multiple sleeves can be produced in parallel through a single compression. This is advantageous, in one embodiment, for example, if the sleeves are to be fabricated in a short time and in large numbers.

Processes according to one embodiment can provide all forming steps, including the punching of the repetitive structures and/or the punching off of the sleeve mold, to take place using a single tool, whereby the tool is being pressed onto the metallic tape, whereby multiple modules are arranged in series one after the other in the tool and a step of reforming or punching off or punching-reforming is carried out with each module.

Presently, being arranged one after the other shall be understood to refer to the conveying direction of the metallic tape that is being conveyed and reformed in the process by the tool.

As a result, the process can be implemented with a compact tool in space-saving manner and rapidly, because of the short conveying distances. Moreover, due to the modular structure of the tool, the tool can be used for large numbers of different sleeves by exchanging individual modules. This reduces the costs associated with conversion of the tool and thus cost of the sleeves, since the tools for punching and/or reforming generate most of the costs.

In this context, one embodiment can provide the tape to be transported on to the next module after each punching and/or reforming, whereby, the distances of all modules with respect to each other in conveying direction of the metallic tape are always the same.

This illustrates how a process for mass production of the sleeves can be implemented. Using the process, large quantities of the sleeves can be fabricated inexpensively in a short time.

Moreover, one embodiment can provide at least four, or at least five, chronologically separate reforming steps to take place in order to generate the sleeve mold, whereby the tool includes at least four modules, or at least five modules, for this purpose.

This ensures that the material of the tape is not excessively stressed to the extent that there is a risk of the tape tearing or forming cracks during each reforming step and/or deep-drawing step the metallic tape, which is carried out with a module.

A refinement of the process according to one embodiment proposes the metallic tape and the sleeves fabricated from it to consist of tantalum, titanium, palladium, platinum, gold or a platinum-iridium alloy, an alloy comprising at least two of the elements tantalum, titanium, palladium, platinum, gold, and iridium or a metallic compound containing gold and/or platinum as its main component.

These materials are in one embodiment for electrophysiological and neuro-medical applications and are easy to process with the process according to one embodiment.

To improve the processing, one embodiment can provide the tape to be annealed before or right after the repetitive structures are punched in, to be annealed at a temperature between 300° C. and 1,000° C., or to be annealed at a temperature between 500° C. and 950° C., or to be annealed at a temperature between 500° C. and 700° C.

This relaxes the grain boundaries in the metallic tape and makes the grain sizes more uniform such that the risk of over-stressing, for example, the risk of crack formation, during the reforming, for example, during the deep-drawing, is being reduced.

According to one embodiment, the process can provide the metallic tape to be produced by rolling, for example, by rolling followed by annealing.

Using this process, the metallic tape can be fabricated in simple manner and inexpensively from a wire or a compact part.

Moreover, one embodiment can provide the thickness of the metallic tape before the repetitive structures are being punched in ranges from 50 µm to 2 mm, or the thickness ranges from 100 µm to 1 mm, or the thickness ranges from 100 µm to 200 µm.

These thicknesses allow the sleeves to be fabricated in matching sizes for electrophysiological and neuro-medical applications. The sleeves then no longer need to be reworked by turning.

Moreover, one embodiment proposes that the surfaces of the repetitive structures include a surface area of between 10 mm$^2$ and 2,000 mm$^2$, or include a surface area of between 50 mm$^2$ and 1,000 mm$^2$.

These sizes also serve the purpose to allow sleeves with a suitable size for electrophysiological and neuro-medical applications to be produced from the tape structured by punching such that the processing generates only little scrap, which would need to be melted again for recycling.

Moreover, one embodiment can provide the wall thickness of the finished sleeve to be between 30 µm and 300 µm.

The wall thicknesses are particularly well-suited for sleeves for electrophysiological and neuro-medical applications.

For the later application of the sleeves produced with the process according to one embodiment, it is provided that at least all outward-facing structures of the sleeve to be produced to have a radius of curvature of more than 0.1 mm, or all structures of the sleeve (1) to be produced to have a radius of curvature of more than 0.1 mm.

As a result, no sharp edges are present in those regions that get connected to the often very fine wires later on. As a result, damage to the wires can be prevented or at least the risk of damage can be reduced. Damage to the wires can have an adverse effect on the function and durability of the product for electrophysiological use, whose design includes the sleeve.

Moreover, one embodiment proposes the first region with the larger diameter to comprise a length of between 1 mm and 20 mm, or between 4 mm and 15 mm, and/or the second region with the smaller diameter to include a length of between 1 mm and 10 mm, or between 2 mm and 8 mm.

By this means, an external connection surface for a sensor is being provided by the external circumference of the first region, and a contact surface and a guidance for an electrical contacting by means of a wire is being provided by the external circumference of the second region. As such, the sleeve thus produced is well-suited for producing the contacting for cardiac pacemakers.

According to one embodiment, the process can provide the external diameter of the first region with the larger diameter to be between 0.5 mm and 5 mm, or between 1 mm and 2.5 mm, and/or the external diameter of the second region with the smaller diameter to be between 0.4 mm and 4.5 mm, or between 0.5 mm and 2 mm.

The dimensions are particularly well-suited for sleeves for pacemakers.

One embodiment of the process can provide the second region with the smaller diameter to have a circumferential flange formed in it for attaching a coil or a wire by welding, whereby the external diameter of the flange is at least 0.1 mm larger than the external diameter of the second region, or is between 0.5 mm and 5 mm larger than the external diameter of the second region.

By this means, a sleeve is being provided to which a wire for electrical contacting of the sleeve can be attached at a defined site, namely the flange. In addition, the flange can be used as a support for a spring system of the wire, if the wire is coiled circumferentially about the second region in the form of a spring. Moreover, the flange can also serve as a boundary preventing further insertion of the sleeve into a hose, for example, a plastic hose.

One embodiment can just as well provide contacting structures, for example, depressions and/or recesses, on the external circumference of the sleeve of the first and/or second region that are suitable for connecting other components by welding, crimping, soldering and/or gluing.

By this means, the sleeve can be connected more easily to further components such as, for example, sensors, wires, tubes or electronic components.

Moreover, one embodiment can provide the sleeve mold to be appropriately reformed during the reforming steps such that the sleeve includes, aside from the first tube-shaped region with the larger diameter and the second tube-shaped region with the smaller diameter, a third tube-shaped region, whereby the third region has a smaller diameter than the first tube-shaped region with the larger diameter, whereby all three regions are connected to each other in one-part manner, for example, are appropriately connected to each other in one-part manner such that the sleeve forms a continuous tube.

By this means, a further variant of a sleeve is being generated, in which a bulge is generated in the middle. Therefore, according to one embodiment, a third region can be provided as well aside from the first region and the second region. In one embodiment, no closed covering surface is provided in this variant.

The objects of one embodiment are also met by a process for producing a neuro-medical sensor or an electrophysiological ring electrode comprising the method, in which a first wire is welded to the flank of the transition from the first region to the second region or on the flange, whereby the first wire extends around the second region of the sleeve helically and extends in the direction away from the first region.

The neuro-medical sensor and/or the electrophysiological ring electrode can be used, for example, for controlling a cardiac pacemaker or a probe for deep brain stimulation. In this case, the first wire can be supported against the flank or the flange in springlike manner. By this means, the motions occurring in the body can be compensated for without intensive mechanical stress acting on the connection between the first wire and the sleeve.

In this context, one embodiment can provide a second wire, for example, a helical second wire, to be drawn through the inside of the sleeve, whereby the second wire is electrically insulated with respect to the sleeve and the first wire.

The second wire can be used as a probe for electrical stimulation of a muscle or nerve cells. By this means, an electrode produced by means of the process can be used as an electrophysiological electrode.

Moreover, one embodiment can provide an electrode for measuring a change of the electrical field strength and/or a contact surface for an electrode for measuring a change of the electrical field strength, which is connected in electrically conductive manner to the first wire, to be attached to the outside of the first region of the sleeve.

By this means, the sleeve can be used in electrophysiological applications as an electrode by means of which a muscular or neurological response can be measured. A sensor including the electrophysiological electrode can then be designed as well.

And lastly, the underlying objects of one embodiment are also met by a sleeve for electrophysiological applications or a neuro-medical sensor or electrophysiological ring electrode produced with the process according to one embodiment.

One embodiment is based on finding, surprisingly, that reforming a metallic tape allows the sleeves to be designed such that there are no major amounts of scrap of the material from which the sleeve is fabricated. Simultaneously, sharp edges can be prevented in such reforming steps, such as deep-drawing steps, and thus the risk of damaging the wires for contacting the produced ring electrode including the sleeve can be reduced. The process according to one embodiment can be implemented quickly and can be implemented inexpensively. The process according to one embodiment is also easy to vary, for example, if a tool containing multiple exchangeable modules is used, by means of which a stepwise further reforming of the tape to the sleeve takes place in individual steps of reforming, for example, deep-drawing steps, punching steps or punching-reforming steps. Since a high degree of reforming is required, one embodiment provides the reforming of the tape to the sleeve to take place in multiple reforming steps, for example, in at least three or at least four reforming steps. This ensures that the reforming does not lead to destruction of the material and/or damage to the generated sleeve. The shape of the sleeve and the material of the sleeve are well-suited for electrophysiological and neuro-medical applications.

The new fabrication approach overcomes the disadvantages of the prior art since it allows a thin tape to be used as starting material and, consequently, this is associated with only low losses of precious metal. Moreover, this process is very inexpensive and yields high-quality and reproducible results. The process according to one embodiment allows for inexpensive production of ring electrodes and components from precious metal or containing at least one precious metal for example in electrophysiology and neuro-medicine, for example, as stimulation or measuring electrode in the field of active implants. Whereas a turning process is subject to extensive variations due to tool wear and tear, a forming process according to one embodiment is significantly more repeatable such that the sleeves produced according to one embodiment are subject to a clearly lower variation and/or deviation between parts.

What is claimed is:

1. A method of producing a sleeve for a ring electrode for electrophysiological and neuro-medical applications from a metallic tape, wherein the tape and the sleeve fabricated from the tape consist of a biocompatible metal or a biocompatible metallic compound, the method comprising:
punching into the tape to define repetitive structures, wherein the repetitive structures each comprise at least one surface that is connected by at least one fin to at least one external strip, wherein at least the at least one external strip connects the repetitive structures to each other on a margin;
subsequently forming a sleeve mold from a multiple of the at least one surfaces of the repetitive structures through multiple reforming steps by deep-drawing; and
punching off the sleeve mold such that the sleeve is formed comprising a first tube-shaped region with a larger diameter and a second tube-shaped region with a smaller diameter, wherein the first region with the larger diameter comprises a larger external diameter and internal diameter than the second region with the smaller diameter, and the two regions are connected to each other such that the sleeve forms a continuous tube characterized in that the second region with the smaller diameter has a circumferential flange formed in it for attaching a coil or a wire by welding, wherein the external diameter of the flange is at least 0.1 mm larger than the external diameter of the second region.

2. The method of claim 1, characterized in that the tape and the sleeve fabricated from the tape consist of a precious metal, titanium, tantalum or a metallic compound thereof or a metallic compound containing at least one precious metal as main component or titanium or tantalum as main component.

3. The method of claim 1, characterized in that the multiple reforming steps of the deep-drawing take place using a single tool, whereby the tool is being pressed onto the metallic tape, whereby multiple modules are arranged in series one after the other in the tool and a step of reforming or punching off or punching-reforming is performed with each module.

4. The method of claim 3, characterized in that the tape is transported a distance on to the next module after each punching and/or reforming, whereby, the distance of all modules with respect to each other in a conveying direction of the metallic tape are equal.

5. The method of claim 3, characterized in that at least four chronologically separate reforming steps take place in order to generate the sleeve mold, wherein the tool comprises at least four modules for this purpose.

6. The method of claim 1, characterized in that the metallic tape and the sleeve fabricated from the tape consist of tantalum, titanium, palladium, platinum, gold or a platinum-iridium alloy, an alloy comprising at least two of the elements tantalum, titanium, palladium, platinum, gold, and iridium or a metallic compound containing gold and/or platinum as its main component.

7. The method of claim 1, characterized in that the tape is being annealed before or right after the repetitive structures are punched in, and is being annealed at a temperature between 300° C. and 1,000° C.

8. The method of claim 1, characterized in that the metallic tape is produced by rolling followed by annealing.

9. The method of claim 1, characterized in that a thickness of the metallic tape before the repetitive structures are being punched is in a range from 50 µm to 2 mm.

10. The method of claim 1, characterized in that the surfaces of the repetitive structures comprise a surface area of between 10 mm$^2$ and 2,000 mm$^2$.

11. The method of claim 1, characterized in that a wall thickness of the sleeve is between 30 µm and 300 µm.

12. The method of claim 1, characterized in that at least all outward-facing structures of the sleeve are produced to have a radius of curvature (R1, R2, R3) of more than 0.1 mm.

13. The method of claim 1, characterized in that the first region with the larger diameter comprises a length of between 1 mm and 20 mm, and the second region with the smaller diameter comprises a length of between 1 mm and 10 mm.

14. The method of claim 1, characterized in that the external diameter of the first region with the larger diameter is between 0.5 mm and 5 mm and the external diameter of the second region with the smaller diameter is between 0.4 mm and 4.5 mm.

15. The method of claim 1, characterized in that depressions and/or recesses are provided on an external circumference of the sleeve of the first and/or second region that are suitable for connecting other components by welding, crimping, soldering and/or gluing.

16. The method of claim 1, characterized in that the sleeve mold is appropriately reformed during the reforming steps such that the sleeve comprises, aside from the first tube-shaped region with the larger diameter and the second tube-shaped region with the smaller diameter, a third tube-shaped region, wherein the third region has a smaller diameter than the first tube-shaped region with the larger diameter, wherein all three regions are connected to each other in one-part manner, in particular are appropriately connected to each other in one-part manner such that the sleeve forms a continuous tube.

17. The method of claim 1, further comprising producing a neuro-medical sensor or an electrophysiological ring electrode by welding a first wire to a flank of a transition from the first region to the second region or on a flange, wherein the first wire extends around the second region of the sleeve helically and extends in a direction away from the first region.

18. The method of claim 17, characterized in that a second helical wire, is drawn through an inside of the sleeve, wherein the second wire is electrically insulated with respect to the sleeve and the first wire.

19. The method of claim 17, characterized in that a sensor for measuring a change of an electrical field strength and/or a contact surface for a sensor for measuring a change of the electrical field strength, which is connected in electrically conductive manner to the first wire, is attached to an outside of the first region of the sleeve.

* * * * *